United States Patent
Naito et al.

(10) Patent No.: US 7,064,221 B2
(45) Date of Patent: Jun. 20, 2006

(54) PROCESS FOR PRODUCING PYRAN

(75) Inventors: Kazuki Naito, Wakayama (JP); Koji Mine, Wakayama (JP)

(73) Assignee: Kao Corporation, Tokyo (JP)

( * ) Notice: Subject to any disclaimer, the term of this patent is extended or adjusted under 35 U.S.C. 154(b) by 33 days.

(21) Appl. No.: 10/915,319

(22) Filed: Aug. 11, 2004

(65) Prior Publication Data

US 2005/0059833 A1  Mar. 17, 2005

(30) Foreign Application Priority Data

Sep. 17, 2003 (JP) ............ 2003-325029

(51) Int. Cl.
*C07D 309/00* (2006.01)
(52) U.S. Cl. .................. 549/356; 549/427
(58) Field of Classification Search ........ 549/356, 549/427
See application file for complete search history.

(56) References Cited

U.S. PATENT DOCUMENTS 3,681,263 A  8/1972  Van Der Linde

FOREIGN PATENT DOCUMENTS

| CH | 655 932 | 5/1986 |
| GB | 1 337 263 | 11/1973 |
| JP | 8-127577 | 5/1996 |
| JP | 11-29564 | 2/1999 |

*Primary Examiner*—Cecilia J. Tsang
*Assistant Examiner*—Raymond Covington
(74) *Attorney, Agent, or Firm*—Oblon, Spivak, McClelland, Maier & Neustadt, P.C.

(57) ABSTRACT

This invention provides a process for producing a pyran efficiently with high productivity and simplified production facilities. The process for producing a pyran comprises reacting aldehyde (I) represented by:

$$R^1\text{—CHO} \qquad (I)$$

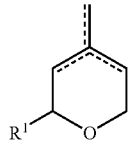

(II)

wherein 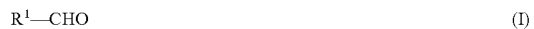 is a single or double bond and $R^1$ represents an alkyl or alkenyl group having 1 to 12 carbon atoms, an optionally alkyl- or alkoxy-substituted aryl group having 6 to 12 carbon atoms in total, etc., to react isoprenol to produce pyran (II), wherein water in a reactor is maintained in an amount of 0.25 wt % or less while the conversion of that which has the lower charged total number of moles between aldehyde (I) and isoprenol is less than 50%.

9 Claims, No Drawings

PROCESS FOR PRODUCING PYRAN

FIELD OF THE INVENTION

The present invention relates to a process for producing a pyran.

BACKGROUND OF THE INVENTION

Pyran is an important industrial raw material of perfume. For example, α-phenyl-dihydropyran can be converted by reductive opening of its pyran ring into 5-phenyl-3-methyl-pentanol particularly important as a perfume. Further, tetrahydro-4-hydroxy-2-isobutyl-4-methyl-pyran itself is useful as a perfume.

Swiss Patent No. 655932 discloses a process for producing a pyran derivative by reacting an aromatic aldehyde with isoprenol in the presence of an acidic dehydrating agent.

JP-A 11-29564 discloses a process for producing a pyran derivative by reacting an aldehyde with a diene compound such as isoprene in the presence of a Lewis acid catalyst.

SUMMARY OF THE INVENTION

The present invention relates to a process for producing a pyran, which includes reacting an aldehyde represented by the formula (I) (hereinafter, referred to as aldehyde (I)):

$$R^1-CHO \quad (I)$$

wherein $R^1$ represents a hydrogen atom, an alkyl or alkenyl group having 1 to 12 carbon atoms, an optionally alkyl-substituted cycloalkyl group having 3 to 12 carbon atoms in total or an optionally alkyl- or alkoxy-substituted aryl group having 6 to 12 carbon atoms in total, with isoprenol to produce a pyran represented by the formula (II):

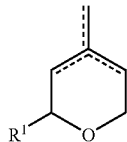

(II)

wherein $R^1$ has the same meaning as defined above, and 
is a single or double bond,
wherein water in a reactor is maintained in an amount of 0.25 wt % or less while the conversion of that which has the lower charged total number of moles between aldehyde (I) and isoprenol is less than 50%.

DETAILED EXPLANATION OF THE INVENTION

In Swiss Patent No. 655932, there is the problem of a reduction in reaction yield of pyran.

In JP-A 11-29564, a halogenated Lewis acid catalyst such as aluminum chloride is used, and therefore a hydrogen halide gas can be generated during the reaction, thus requiring corrosion-resistant production facilities. The diene compound, such as isoprene, described in JP-A 11-29564 is highly flammable and polymerizable, thus requiring facilities kept at low temperatures.

The present invention provides a process for producing a pyran efficiently with high productivity and simplified production facilities.

According to the process of the present invention, pyran that is an important industrial raw material of perfume can be produced efficiently and economically with simplified production facilities.

In the invention, the amount of water in a reactor is an amount determined by a Karl Fisher coulometric titration method (trace-water measuring instrument AQ-7 manufactured by Hiranuma Sangyo Co., Ltd.), and the conversion of aldehyde (I) is a value defined by equation (1) below and the conversion of isoprenol is a value defined by equation (2) below.

$$\text{Conversion of aldehyde }(I) = \frac{\text{number of moles of aldehyde }(I)\text{ converted in a reactor}}{\text{number of moles of added aldehyde }(I)\text{ in total}} \times 100 \quad (1)$$

$$\text{Conversion of isoprenol} = \frac{\text{number of moles of isoprenol converted in a reactor}}{\text{number of moles of added isoprenol in total}} \times 100 \quad (2)$$

In aldehyde (I) used in the present invention, $R^1$ represents a hydrogen atom, an alkyl or alkenyl group having 1 to 12 carbon atoms, an optionally alkyl-substituted cycloalkyl group having 3 to 12 carbon atoms in total, or an optionally alkyl- or alkoxy-substituted aryl group having 6 to 12 carbon atoms in total, preferably an alkyl group having 3 to 12 carbon atoms or an optionally alkyl-substituted aryl group having 6 to 12 carbon atoms in total, more preferably an optionally alkyl-substituted aryl group having 6 to 12 carbon atoms in total, even more preferably a phenyl group or an o-, m- or p-tolyl group.

Examples of aldehyde (I) include benzaldehyde, o-, m- or p-tolualdehyde, naphthoaldehyde, butylaldehyde, valeraldehyde, capronaldehyde, heptaldehyde, caprylaldehyde, caprinaldehyde, laurinaldehyde etc., among which benzaldehyde and o-, m- or p-tolualdehyde are preferable, and benzaldehyde is particularly preferable.

Isoprenol used in the present invention, which can be easily produced by reacting isobutylene with formaldehyde, is a compound represented by formula (III):

(III)

From the viewpoint of improving the yield of pyran, the reaction in the present invention is carried out such that water in a reactor is maintained in an amount of 0.25 wt % or less, preferably 0.2 wt % or less, while the conversion of that which has the lower charged total number of moles between aldehyde (I) and isoprenol is less than 50%.

From the viewpoint of further improving the yield of pyran, water in the reactor is maintained preferably in an amount of 0.25 wt % or less, particularly 0.15 wt % or less, from the start of the reaction to the end of the reaction.

The reaction is carried out by (1) a method that involves charging a reactor with a solvent and a catalyst and then adding aldehyde (I) and isoprenol dropwise thereto, (2) a method that involves charging a reactor with a solvent, a catalyst and aldehyde (I) and then adding isoprenol dropwise thereto, (3) a method that involves charging a reactor with a solvent, a catalyst and isoprenol and then adding aldehyde (I) dropwise thereto, and (4) a method that involves charging a reactor with a solvent, aldehyde (I) and isoprenol and then initiating the reaction, among which the method (1) or (2) is preferable from the viewpoint of improving the yield of pyran. The reaction is carried out preferably by a method wherein water formed in the reaction is distilled away together with a solvent, and after the water is separated from the solvent with a dehydrating tube or the like, the solvent is returned to the reactor. Water in the solvent should be removed when the reaction yield is lowered due to a very small amount of water in the solvent, and water can be removed by a reaction method that involves heating the solvent to remove water and returning the solvent to a reactor, a reaction method that involves returning the solvent to an upper part of a distillating column attached to a reactor, or a reaction method that involves feeding a water-free solvent in an amount equal to that of the solvent which was distilled away.

The solvent used in the present invention is preferably a hydrocarbon solvent such as toluene, heptane and cyclohexane, more preferably toluene. The weight ratio of the solvent to finally charged aldehyde (I) and isoprenol, that is, the solvent/[aldehyde (I)+isoprenol], is preferably 0.2 to 2, more preferably 0.2 to 1.

In the present invention, the final molar ratio of aldehyde (I) to isoprenol may be selected such that aldehyde (I) is in excess or isoprenol is in excess, but from the viewpoint of improvement in the yield of pyran, aldehyde (I)/isoprenol (molar ratio) is preferably 0.5 to 10, more preferably 0.5 to 3.5.

The catalyst used in the reaction of the present invention includes methanesulfonic acid, p-toluenesulfonic acid, sulfuric acid, hydrochloric acid etc., among which methanesulfonic acid and p-toluenesulfonic acid are preferable. The amount of the catalyst added is preferably 0.05 to 5 mol-%, more preferably 0.1 to 5 mol-%, relative to aldehyde (I).

The reaction in the present invention is carried out at a temperature of the boiling point of the solvent or more. The reaction temperature cannot be specified because the boiling point of the solvent is varied depending on the type of solvent used and the reaction pressure, but from the viewpoint of increasing the reaction rate, the reaction temperature is preferably 20 to 120° C., more preferably 40 to 120° C. The reaction is carried out preferably in such conditions that the solvent distilled away outside of the reactor is efficiently condensed, and returned to the reactor. For this purpose, the reaction pressure is preferably 0.5 to 101.3 kPa, more preferably 5 to 101.3 kPa.

The amount of water in the reactor can be regulated by suitably regulating the rate of distilling the solvent away and the rate of formation of water. In order to regulate the amount of water in the range defined above, it is preferable that the ratio of the solvent-distilling rate to the water-forming rate is 100 to 2000, more preferably 150 to 1000, while the conversion of that which has the lower total charged number of moles between aldehyde (I) and isoprenol is less than 50%. In the viewpoint of improved production yield of pyran, it is preferably that the ratio of the solvent-distilling rate to the water-forming rate is 100 to 2000, more preferably 150 to 1000 from the start of the reaction to the end of the reaction.

The rate of formation of water can be regulated by suitably regulating the time of dropwise addition of aldehyde (I) and isoprenol, the reaction temperature and the amount of the catalyst. The time of dropwise addition is preferably 1 hour or more from the view point of inhibiting formation of byproducts, or is preferably 48 hours or less in consideration of productivity. Accordingly, the time of dropwise addition is preferably 1 to 48 hours, more preferably 1 to 24 hours. The reaction temperature is preferably 40° C. or more from the viewpoint of increasing the reaction rate or is preferably 120° C. or less from the view point of inhibiting formation of byproducts. Accordingly, the reaction temperature is preferably 40 to 120° C., more preferably 40 to 80° C.

In the reaction of the present invention, after aldehyde (I) and isoprenol are added dropwise, which may be followed by aging if necessary to further increase the conversion. The temperature and pressure during aging may, in principle, be the same as when the raw materials are added dropwise. The aging time is not particularly limited, but is preferably about 1 to 12 hours because the decomposition, polymerization etc. of the reaction product proceeds as the aging time is increased.

EXAMPLES

In the Examples below, the yield of dihydrophenyl pyran was determined by equation (3) below in Examples 1 to 3 and Comparative Example 1 and by equation (4) below in Comparative Example 2. The rate of formation of water was determined by equation (5) below.

$$\text{Yield of dihydrophenyl pyran} = \frac{\text{number of moles of formed dihydrophenyl pyran}}{\text{number of moles of added benzaldehyde in total}} \times 100 \quad (3)$$

$$\text{Yield of dihydrophenyl pyran} = \frac{\text{number of moles of formed dihydrophenyl pyran}}{\text{number of moles of added isoprenol in total}} \times 100 \quad (4)$$

$$\text{Rate of formation of water} = \frac{(B1 - B2) \times 18.02}{\text{Reaction time}} \quad (5)$$

In formula (5), B1 is the number of moles of added benzaldehyde, and B2 is the number of moles of benzaldehyde remaining in the reactor.

Example 1

A 300 ml four-necked flask equipped with a dehydrating tube was charged with 80.1 g (0.869 mol) toluene and 1.43 g (0.0075 mol) p-toluenesulfonic acid, and the raw materials were mixed at room temperature. The pressure in the reactor was evacuated to a pressure of 13.3 kPa, and then the reactor was placed in an oil bath having temperature control and heated until the temperature in the reactor reached 51° C. Then, a mixture prepared at room temperature by mixing 80.0 g (0.754 mol) benzaldehyde with 71.5 g (0.830 mol) isoprenol was added dropwise to the four-necked flask over 4 hours. After dropwise addition was finished, the reaction mixture was kept for 8 hours (called aging) under the same condition except for addition of isoprenol. During the dropwise addition and aging, the mixture was stirred, the temperature of the oil bath was controlled at 73 to 88° C., toluene and water formed by the reaction were distilled away, the toluene was separated from the water in the dehydrating tube, and the toluene only was returned to the reactor. In this reaction, the ratio of the rate of distilling toluene away to the amount of the initially charged toluene, until the conversion of benzaldehyde was 18.2%, was 2.7 (1/h) on the average. The rate of distilling toluene away was 216.3 g/h and the rate of formation of water was 1.12 g/h. The ratio of the rate of distilling toluene away to the rate of formation of water was 193.

As a result, the changes in the amount of water in a reactor, the conversion of benzaldehyde, and the yield of dihydrophenyl pyran represented by formula (IV) during the reaction were as shown in Table 1, and when the aging was finished, 114.4 g (0.657 mol) dihydrophenyl pyran was obtained in 87.1% yield (based on benzaldehyde charged).

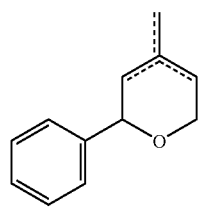

(IV)

TABLE 1

| Reaction time [hr] | Conversion of benzaldehyde [%] | Amount of water in reactor[%] | Yield of dihydrophenyl pyran [%] |
| --- | --- | --- | --- |
| 2.2 | 18.2 | 0.110 | 14.8 |
| 4.0 | 56.2 | 0.117 | 32.3 |
| 9.0 | 86.0 | 0.025 | 79.0 |
| 12.0 | 97.9 | 0.015 | 87.1 |

Example 2

A 500 ml four-necked flask equipped with a dehydrating tube was charged with 90.3 g (0.980 mol) toluene and 1.61 g (0.0085 mol) p-toluenesulfonic acid, and the materials were mixed at room temperature. The air pressure in the reactor was evacuated to a pressure of 13.3 kPa, and then the reactor was placed in a temperature control oil bath and heated until the temperature in the reactor reached 51° C. Then, a mixture prepared at room temperature by mixing 90.0 g (0.848 mol) benzaldehyde with 80.4 g (0.933 mol) isoprenol was added dropwise to the four-necked flask over 15.8 hours. After dropwise addition was finished, the reaction mixture was kept for 5.5 hours under the same conditions excpept for addition of isoprenol (aging). During the dropwise addition and aging, the mixture was stirred. The temperature of the oil bath was controlled at 59 to 73° C., toluene and water formed by the reaction were distilled away, the toluene was separated from the water in the dehydrating tube, and the toluene only was returned to the reactor. In this reaction, the ratio of the rate of distilling toluene away to the amount of toluene charged, until the conversion of benzaldehyde was 8.2%, was 0.48 (1/h) on the average. The rate of distilling toluene away was 43.3 g/h, and the rate of formation of water was 0.25 g/h, and thus the ratio of the rate of distilling toluene away to the rate of formation of water was 172.

As a result, the changes in the amount of water in a reactor, the conversion of benzaldehyde, and the yield of dihydrophenyl pyran during the reaction were as shown in Table 2, and when the aging was finished, 121.3 g (0.696 mol) dihydrophenyl pyran was obtained in 82.1% yield (based on benzaldehyde charged).

TABLE 2

| Reaction time [hr] | Conversion of benzaldehyde [%] | Amount of water in rector [%] | Yield of dihydrophenyl pyran [%] |
| --- | --- | --- | --- |
| 5.0 | 8.2 | 0.161 | 11.1 |
| 10.0 | 33.5 | 0.187 | 27.8 |
| 15.8 | 75.6 | 0.126 | 57.0 |
| 18.1 | 87.0 | 0.132 | 70.9 |
| 21.3 | 97.1 | 0.080 | 82.1 |

Example 3

A 300 ml four-necked flask equipped with a dehydrating tube was charged with 50.1 g (0.544 mol) toluene and 0.90 g (0.0094 mol) methanesulfonic acid, and the materials were mixed at room temperature. The air pressure in the reactor was evacuated to 13.3 kPa, and then the reactor was placed in a temperature control oil bath and heated until the temperature in the reactor reached 51° C. Then, a mixture prepared at room temperature by mixing 50.0 g (0.471 mol) benzaldehyde with 44.7 g (0.519 mol) isoprenol was added dropwise to the four-necked flask over 4.2 hours. After dropwise addition was finished, the reaction mixture was kept for 6 hours under the same condition except for addition of isoprenol (aging). During the dropwise addition and aging, the mixture was stirred, the temperature of the oil bath was controlled at 77 to 81° C., toluene and water formed by the reaction were distilled away, the toluene was separated from the water in the dehydrating tube, and the toluene only was returned to the reactor. In this reaction, the ratio of the rate of distilling toluene away to the amount of toluene charged, until the conversion of benzaldehyde was 10.2%, was 3.8 (1/h) on the average. The rate of distilling toluene away was 190.4 g/h, and the rate of formation of water was 0.58 g/h, and thus the ratio of the rate of distilling toluene away to the rate of formation of water was 329.

As a result, the changes in the amount of water in a reactor, the conversion of benzaldehyde, and the yield of dihydrophenyl pyran during the reaction were as shown in Table 3, and when the aging was finished, 67.2 g (0.386 mol) dihydrophenyl pyran was obtained in 82.0% yield (based on benzaldehyde charged).

TABLE 3

| Reaction time [hr] | Conversion of benzaldehyde [%] | Amount of water in rector [%] | Yield of dihydrophenyl pyran [%] |
| --- | --- | --- | --- |
| 1.5 | 10.2 | 0.130 | 16.9 |
| 3.0 | 36.8 | 0.219 | 30.1 |
| 4.2 | 61.0 | 0.185 | 40.2 |
| 6.2 | 79.6 | 0.085 | 60.8 |
| 8.2 | 90.1 | 0.099 | 75.7 |
| 10.2 | 98.0 | 0.047 | 82.0 |

Comparative Example 1

A 500 ml four-necked flask equipped with a dehydrating tube was charged with 80.8 g (0.877 mol) toluene and 1.46 g (0.015 mol) methanesulfonic acid, and the materials were mixed at room temperature. The air pressure in the reactor was evacuated to 13.3 kPa, and then the reactor was placed in a temperature control oil bath and heated until the temperature in the reactor reached 51° C. Then, a mixture prepared at room temperature by mixing 80.0 g (0.754 mol) benzaldehyde with 71.5 g (0.830 mol) isoprenol was added dropwise to the four-necked flask over 4 hours. After dropwise addition was finished, the reaction mixture was kept for 5.5 hours under the same condition except for addition of isoprenol (aging). During the dropwise addition and aging, the mixture was stirred, the temperature of the oil bath was controlled at 55 to 60° C., toluene and water formed by the reaction were distilled away, the toluene was separated from the water in the dehydrating tube, and the toluene only was returned to the reactor. In this reaction, the ratio of the rate of distilling toluene away to the amount of toluene charged, until the conversion was 22.6%, was 0.45 (1/h) on the average. The rate of distilling toluene away was 36.4 g/h, and the rate of formation of water was 1.23 g/h, and thus the ratio of the rate of distilling toluene away to the rate of formation of water was 30.

As a result, the changes in the amount of water in a reactor, the conversion of benzaldehyde, and the yield of dihydrophenyl pyran during the reaction were as shown in Table 4, and when the aging was finished, 94.2 g (0.541 mol) dihydrophenyl pyran was obtained in 71.8% yield (based on benzaldehyde charged).

TABLE 4

| Reaction time [hr] | Conversion of benzaldehyde [%] | Amount of water in reactor [%] | Yield of dihydrophenyl pyran [%] |
| --- | --- | --- | --- |
| 2.5 | 22.6 | 0.287 | 17.8 |
| 4.0 | 52.6 | 0.296 | 31.3 |
| 6.0 | 73.7 | 0.147 | 50.2 |
| 8.0 | 86.6 | 0.101 | 64.3 |
| 9.5 | 93.6 | 0.057 | 71.8 |

Comparative Example 2

A 500 ml four-necked flask equipped with a dehydrating tube was charged with 75.0 g (0.814 mol) toluene and 1.81 g (0.019 mol) methanesulfonic acid, and the materials were mixed at room temperature. The air pressure in the reactor was evacuated to a pressure of 13.3 kPa, and then the reactor was placed in a temperature control oil bath and heated until the temperature in the reactor reached 51° C. Then, a mixture prepared at room temperature by mixing 100.0 g (0.942 mol) benzaldehyde with 44.7 g (0.519 mol) isoprenol was added dropwise to the four-necked flask over 4.2 hours. After dropwise addition was finished, the reaction mixture was kept for 3 hours under the same condition except for addition of isoprenol (aging). During the dropwise addition and aging, the mixture was stirred, the temperature of the oil bath was controlled at 65 to 76° C., toluene and water formed by the reaction were distilled away, the toluene was separated from the water in the dehydrating tube, and the toluene only was returned to the reactor. In this reaction, the ratio of the rate of distilling toluene away to the amount of toluene charged, until the conversion of isoprenol was 29.2%, was 1.6 (1/h) on the average. The rate of distilling toluene away was 120.0 g/h, and the rate of formation of water was 1.71 g/h, and thus the ratio of the rate of distilling toluene away to the rate of formation of water was 70.

As a result, the changes in the amount of water in a reactor, the conversion of isoprenol, and the yield of dihydrophenyl pyran during the reaction were as shown in Table 5, and when the aging was finished, 58.7 g (0.337 mol) dihydrophenyl pyran was obtained in 64.9% yield (based on isoprenol charged).

TABLE 5

| Reaction time [hr] | Conversion of isoprenol [%] | Amount of water in reactor [%] | Yield of dihydrophenyl pyran [%] |
| --- | --- | --- | --- |
| 2.0 | 29.2 | 1.033 | 29.1 |
| 4.2 | 83.3 | 1.006 | 56.8 |
| 6.2 | 100.0 | 0.876 | 69.8 |
| 8.2 | 100.0 | 0.301 | 64.9 |

The invention claimed is:

1. A process for producing a pyran, which comprises reacting an aldehyde represented by the formula (I) (hereinafter, referred to as aldehyde (I)):

$$R^1\text{—CHO} \quad (I)$$

wherein $R^1$ represents a hydrogen atom, an alkyl or alkenyl group having 1 to 12 carbon atoms, an optionally alkyl-substituted cycloalkyl group having 3 to 12 carbon atoms in total or an optionally alkyl- or alkoxy-substituted aryl group having 6 to 12 carbon atoms in total, with isoprenol to produce a pyran represented by the formula (II):

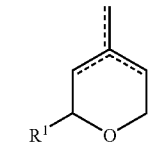

(II)

wherein $R^1$ has the same meaning as defined above, and  is a single or double bond,
wherein water in a reactor is maintained in an amount of 0.25 wt % or less while the conversion of that which has the lower charged total number of moles between aldehyde (I) and isoprenol is less than 50%.

2. The process according to claim 1, wherein water is maintained in an amount of 0.25 wt % or less in a reactor during the reaction.

3. The process according to claim 1 or 2, wherein $R^1$ is an optionally alkyl-substituted aryl group having 6 to 12 carbon atoms in total.

4. The process according to any one of claim 1, which comprises charging a reactor with a solvent and a catalyst, and then adding aldehyde (I) and isoprenol dropwise to a reactor.

5. The process according to any one of claim 1, which comprises charging a reactor with a solvent, a catalyst, and then aldehyde (I) and adding isoprenol dropwise to a reactor.

6. The process according to any one of claims 4 to 5, wherein the ratio of the solvent-distilling rate to the water-forming rate is 100 to 2000 while the conversion of that which has the lower total charged number of moles between aldehyde (I) and isoprenol is less than 50%.

7. The process according to any one of claims 4 to 5, wherein at least one selected from toluene, heptane and cyclohexane is used as the solvent.

8. The process according to any one of claims 4 to 5, wherein at least one selected from methanesulfonic acid and p-toluenesulfonic acid is used as the catalyst.

9. The process according to any one of claims 4 to 5, wherein the weight ratio of the solvent to finally charged aldehyde (I) and isoprenol is 0.2 to 2 in term of solvent/ [aldehyde (I)+isoprenol].

* * * * *